US008903037B2

(12) United States Patent
Yu et al.

(10) Patent No.: US 8,903,037 B2
(45) Date of Patent: Dec. 2, 2014

(54) SYSTEM AND METHOD FOR AUTOMATIC TUBE POTENTIAL SELECTION FOR DOSE REDUCTION IN MEDICAL IMAGING

(71) Applicants: Lifeng Yu, Byron, MN (US); Cynthia H. McCollough, Byron, MN (US); Joel G. Fletcher, Oronoco, MN (US); Hua Li, Chesterfield, MO (US)

(72) Inventors: Lifeng Yu, Byron, MN (US); Cynthia H. McCollough, Byron, MN (US); Joel G. Fletcher, Oronoco, MN (US); Hua Li, Chesterfield, MO (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/183,639

(22) Filed: Feb. 19, 2014

(65) Prior Publication Data
US 2014/0177784 A1 Jun. 26, 2014

Related U.S. Application Data

(63) Continuation of application No. 13/384,454, filed as application No. PCT/US2010/042152 on Jul. 15, 2010, now Pat. No. 8,699,658.

(60) Provisional application No. 61/225,818, filed on Jul. 15, 2009.

(51) Int. Cl.
*A61B 6/03* (2006.01)
*A61B 6/00* (2006.01)

(52) U.S. Cl.
CPC . *A61B 6/03* (2013.01); *A61B 6/032* (2013.01); *A61B 6/481* (2013.01); *A61B 6/504* (2013.01); *A61B 6/544* (2013.01); *A61B 6/545* (2013.01); *A61B 6/405* (2013.01); *A61B 6/542* (2013.01)
USPC .............................................................. 378/8

(58) Field of Classification Search
CPC ......... A61A 6/03; A61A 6/405; A61A 6/542; A61A 6/544
See application file for complete search history.

(56) References Cited

U.S. PATENT DOCUMENTS

| 5,400,378 | A  | 3/1995  | Toth          |
| 5,949,811 | A  | 9/1999  | Baba et al.   |
| 6,094,468 | A  | 7/2000  | Wilting et al.|
| 6,233,310 | B1 | 5/2001  | Relihan et al.|
| 6,459,765 | B1 | 10/2002 | Ganin et al.  |
| 6,775,352 | B2 | 8/2004  | Toth et al.   |

(Continued)

FOREIGN PATENT DOCUMENTS

| EP | 1875865 A2 | 1/2008 |
| EP | 2022402 A1 | 2/2009 |

OTHER PUBLICATIONS

The International Search Report and Written Opinion as mailed on Sep. 14, 2010 for International Application No. PCT/US2010/042152.

(Continued)

*Primary Examiner* — Irakli Kiknadze
(74) *Attorney, Agent, or Firm* — Quarles & Brady, LLP (57) ABSTRACT

A method for CT imaging that utilizes an automatic tube potential selection for individual subjects and diagnostic tasks. The method quantifies the relative radiation dose of different tube potentials for achieving a specific image quality. This allows the selection of a tube potential that provides a reduced radiation dose while still providing CT images of a sufficient quality.

20 Claims, 2 Drawing Sheets

(56) References Cited

U.S. PATENT DOCUMENTS

| | | |
|---|---|---|
| 7,606,345 B2 * | 10/2009 | Nishide et al. .................. 378/4 |
| 7,639,776 B2 * | 12/2009 | Gohno et al. .................. 378/15 |
| 2004/0032928 A1 | 2/2004 | Toth et al. |
| 2004/0062341 A1 | 4/2004 | Popescu et al. |
| 2004/0136498 A1 | 7/2004 | Omernick et al. |
| 2005/0053190 A1 | 3/2005 | Gohno |
| 2005/0169420 A1 | 8/2005 | Edic et al. |
| 2006/0233294 A1 | 10/2006 | Bontus et al. |
| 2006/0285634 A1 | 12/2006 | Toth |
| 2007/0140428 A1 | 6/2007 | Toth |
| 2008/0240336 A1 | 10/2008 | Miyazaki et al. |
| 2009/0046833 A1 | 2/2009 | Hirokawa et al. |
| 2009/0141854 A1 | 6/2009 | Hirokawa et al. |
| 2012/0002781 A1 | 1/2012 | Graham et al. |

OTHER PUBLICATIONS

McCollough, et al., Strategies for Reducing Radiation Dose in CT, Radiol Clin North Am. Jan. 2009 [retrieved on Aug. 25, 2010]. Retrieved from the internet: <URL: http://www.ncbi.nlm.nih.gov/pmc/articles/PMC2743386/pdf/nihms131985.pdf> entire document.

Young, et al., Effect of automatic kV selection on dose and contrast for a mammogrammic X-ray system. The British Journal of Radiology 1997 [retrieved on Aug. 25, 2010]. Retrieved from the internet: <URL: http://bjr.birjournals.org/cgi/reprint/70/838/1036.pdf> entire document.

Yu, Lifeng, et al., Automatic selection of tube potential for radiation dose reduction in CT: A general strategy, Am. Assoc. Phus. Med. 2010, Med. Phys. 37 (1) Jan. 2010, pp. 234-243.

European Patent Office, Supplementary European Search Report, Application No. EP 10 80 0551, Nov. 7, 2013, 2 pages.

* cited by examiner

SYSTEM AND METHOD FOR AUTOMATIC TUBE POTENTIAL SELECTION FOR DOSE REDUCTION IN MEDICAL IMAGING

CROSS-REFERENCE TO RELATED APPLICATIONS

The present application is a continuation of U.S. application Ser. No. 13/384,454, filed Jan. 17, 2012, which is a U.S. National Stage Application of International Application No. PCT/US10/042152, filed Jul. 15, 2010, which is based on U.S. Provisional Patent Application Ser. No. 61/225,818, entitled "METHOD FOR AUTOMATIC kV SELECTION FOR DOSE REDUCTION IN CT," and filed Jul. 15, 2009. The benefit of each of the foregoing is claimed herein and each of the foregoing is incorporated herein by reference in its entirety.

BACKGROUND OF THE INVENTION

The field of the invention is x-ray computed tomography (CT) and, in particular, the selection of CT system parameters for reducing radiation dose.

X-ray imaging exposes individuals to ionizing radiation while being imaged. This radiation dose has become an important concern for public health. While CT has played a dramatic role in the detection and staging of disease, subjects are at a small but increased risk of radiation-induced malignancy. The most frequently employed method to reduce radiation dose is to lower the x-ray tube current using subject size or weight-based protocols. Another important and related dose reduction technique is automatic exposure control (AEC), which involves the automatic adaptation of the tube current during the CT scan. That is, as the CT gantry rotates around the subject and as the subject travels through the gantry, the tube current is adjusted according to subject size to keep image noise and quality constant. While this widely-used approach can achieve a dose reduction of 40-50% without sacrificing image quality, there are still other considerations that could lead to further dose optimization.

Recently, there have been several physics and clinical studies on the use of lower tube potential, which is generally measured using peak-kilovoltage, denoted "kV" or "kVp", CT imaging, with the purpose of improving image quality or further reducing radiation dose. A principle behind this is that iodine has increased attenuation, or CT contrast, at lower tube potentials than at higher tube potentials in the range of tube potentials available on CT scanners. In many CT exams using iodinated contrast media, to achieve the superior enhancement of iodine at lower tube potentials, improves the conspicuity of hypervascular or hypovascular pathologies owing to the differential distribution of iodine, for example, in renal and hepatic masses, and inflamed bowel segments.

Images obtained at lower tube potentials tend to be noisier, primarily due to the higher absorption of low-energy photons by the subject. Therefore, a tradeoff exists between image noise and contrast enhancement in determining the clinical value of lower tube potential. When subject size is above a particular threshold, the benefit of the improved contrast enhancement is negated by the increased noise level. In this situation, the lower tube potential may not generate better image quality than the higher tube potential for the same radiation dose. In other words, dose reduction may not be achieved with the lower tube potential because the higher tube potential is needed to maintain appropriate image quality. However, below this size threshold, various degrees of dose reduction or image quality improvement at the same dose can be achieved. Therefore, for a given subject size and clinical application, an optimal tube potential exists that yields the best image quality or the lowest radiation dose.

Existing clinical studies have used empirically-determined tube potentials for a certain patient group, with various levels of dose reduction or image quality improvement being observed. However, an exact knowledge of the dose-efficiency of different tube potentials to obtain a target image quality, and the dependence of the optimal tube potential on patient size and diagnostic task, remain to be quantitatively determined. In a more recent study, some have used a dose-normalized contrast to noise ratio (CNR) as the criterion to determine the optimal tube potential and to quantify its dependence on phantom sizes and contrast materials. Their results demonstrated that the selection of tube potential should to be adapted to the patient size and to the diagnostic task to a much higher degree than is common practice today in order to further reduce the radiation dose. However, clinical practices to prospectively select the optimal tube potential and determine the corresponding radiation dose level that takes into account both the patient size and the target image quality required by a particular diagnostic task are lacking.

SUMMARY OF THE INVENTION

The present invention overcomes the aforementioned drawbacks by providing a system and method that allows automatic adaptation of tube potential as a function of patient size and diagnostic task and uses a novel image quality index, "noise-constrained iodine contrast to noise ratio," to quantify the different levels of image quality suitable for various clinical applications.

In particular, the present invention provides a method for performing computer tomography (CT) imaging with automatic tube potential selection. This method includes positioning a subject to be imaged in a CT system, selecting a scanning technique at a reference tube potential corresponding to a desired image quality level, and selecting a noise constraint parameter according to the diagnostic task. The method further includes determining the dose efficiency of each tube potential using characteristics of the subject and noise constraint parameter, and performing a CT scan using the most dose-efficient tube potential, provided that the system power limit is not exceeded and the scanning time is practical.

Various other features of the present invention will be made apparent from the following detailed description and the drawings.

DESCRIPTION OF THE PREFERRED EMBODIMENT

Figure 1A:
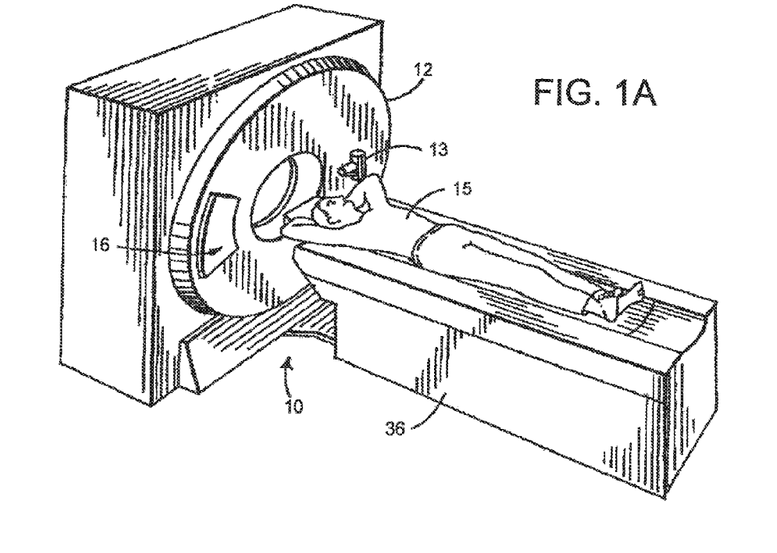
FIGS. 1A and 1B depict a CT system configured to employ an automatic tube potential selection method in accordance with the present invention.
Figure 1B:
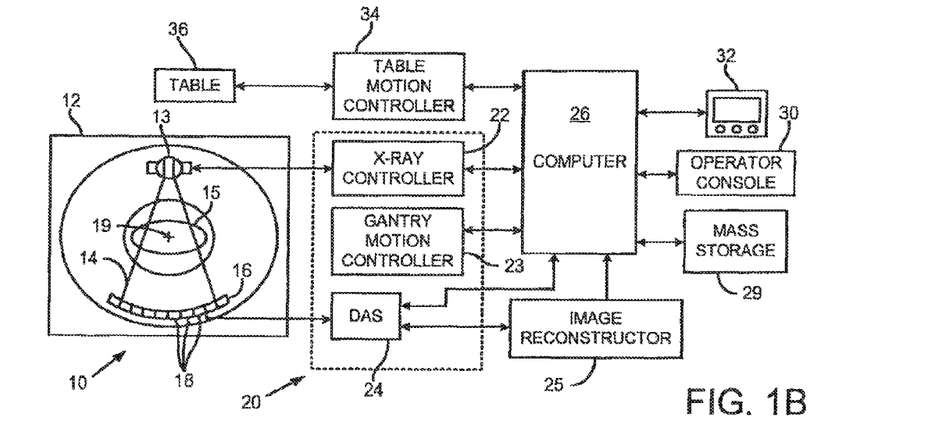

With initial reference to FIGS. 1A and 1B, the present invention may be implemented using a computed tomography (CT) imaging system 10 that includes a gantry 12 and is representative of a "third generation" CT scanner, though the present invention can be implemented on any generation of CT scanner. Gantry 12 has an x-ray source 13 that projects a fan beam or cone beam of x-rays 14 toward a detector array 16 on the opposite side of the gantry. The detector array 16 is formed by a number of detector elements 18 which together sense the projected x-rays that pass through a medical subject 15. Each detector element 18 produces an electrical signal that represents the intensity of an impinging x-ray beam and hence the attenuation of the beam as it passes through the subject. During a scan to acquire x-ray projection data, the gantry 12 and the components mounted thereon rotate about a center of rotation 19 located within the subject 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the subject 15 in the gantry 12.

The present invention provides a method for selecting tube potential in a CT system to reduce radiation dose. Specifically, referring now to FIG. 2, an automatic tube potential selection method using the system, for example, of FIGS. 1A and 1B is provided that uses a dose efficiency evaluation process to achieve dose reduction. The method begins at process block 202 with the acquisition of a scanned projection radiograph, which provides a basis for both automatic tube current modulation and automatic tube potential selection.

Figure 2:
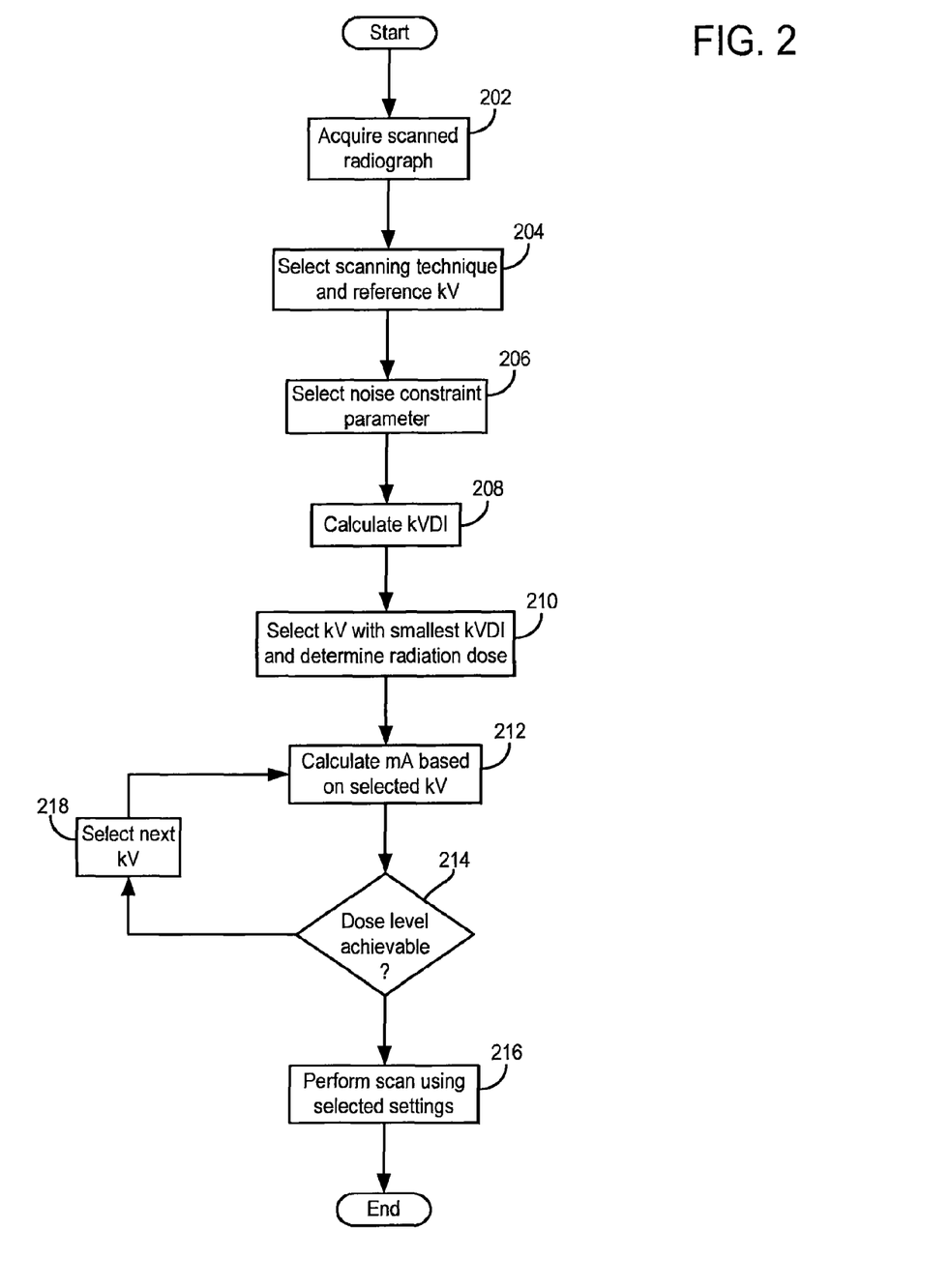
FIG. 2 is a flowchart setting for the steps for an automatic tube potential selection method in accordance with the present invention.

In conventional automatic tube current modulation, the tube current is modulated according to the attenuation level of the subject at each projection angle. The purpose of the modulation is to use appropriate tube current to generate a desired noise level in the CT images. Therefore, the noise level is an image quality index that is used in automatic tube current modulation.

X-ray attenuation can be defined as $A(d) = \exp(\mu d)$ and a general simplified tube current modulation model that relates the tube current to attenuation path length d can be given by:

$$I(d) = I(d_0) \cdot \left( \frac{A(d)}{A(d_0)} \right)^x; \qquad \text{Eqn. 1}$$

where $I(d)$ and $I(d_0)$ respectively denote the tube current for attenuation path length d and $d_0$, which is the reference attenuation path length for which the reference tube current $I(d_0)$. In addition, $\mu$ denotes the average linear attenuation coefficient along the path length and x is the tube current modulation strength. When x=1, a constant noise $\sigma(d_0)$ is maintained in each projection independent of path length. When x<1, the noise level is lower than $\sigma(d_0)$ when the attenuation path length is less than the reference length $d_0$ and higher than $\sigma(d_0)$ when the attenuation path length is longer than the reference length $d_0$.

Noise in each set of projection data (indexed by i) after logarithmic operation can be related to the incident number of photons and attenuation by:

$$\sigma_i^2 = \frac{A_i}{N_{0i}}; \qquad \text{Eqn. 2}$$

wherein $N_{0i}$, is assumed to be proportional to the tube current.

Therefore, with the tube current modulation defined in Eqn. 1, the noise in projection data with an attenuation path length of d is given by:

$$\sigma(d) = \sigma(d_0) \cdot \left( \frac{A(d)}{A(d_0)} \right)^{(1-x)/2}. \qquad \text{Eqn. 3}$$

The relationship between image noise and the noise in the projection data is generally a complicated function that is dependent on the reconstruction algorithm and smoothing filter. This can be simplified by considering only the pixel noise in the center of the image, which can be related to the noise in each projection as:

$$\sigma^2(\Omega_d) = \sum_{i=1}^{N} \sigma^2(d_i); \qquad \text{Eqn. 4}$$

where $\Omega_d = \{d_i | i=1, \ldots, N\}$ denotes a given subject size and $d_i$ is the x-ray path length passing through the isocenter at the i-th projection view. This provides a simplified representation of the subject size. Using a simplified model, some concluded that the minimum image noise is obtained when the modulation strength x is 0.5 for a given total radiation dose, that is, a fixed total number of incident photons.

Contrast-to-noise ratio (CNR) may also be used as an image quality index. If the attenuation of the contrast material along each projection remains the same at $\exp(\mu_c d_c)$, then the contrast in sinogram space is $C = (\mu_c - \mu_w) d_c$, which is independent of the background path length d. Therefore, the CNR in the projection is given by:

$$CNR(d) = \frac{(\mu_c - \mu_w) d_c}{\sigma(d)}. \qquad \text{Eqn. 5}$$

When the tube potential is fixed, the contrast is fixed. Therefore, using CNR as an image quality index to modulate the tube current is equivalent to using noise as the image quality index. When tube potential can also be modulated for each projection view, the contrast is a function of tube potential, which is given by $C(kV) = [\mu_c(kV) - \mu_w(kV)] d_c$. The CNR in a projection can thus be expressed as:

$$CNR(d, kV) = \frac{[\mu_c(kV) - \mu_w(kV)] d_c}{\sigma(d, kV)}. \qquad \text{Eqn. 6}$$

The case in which the CNR at different tube potentials is the same as in a reference tube potential for each path length d may be expressed as follows:

$$CNR(d,kV)=CNR(d,kV_{ref}) \qquad \text{Eqn. 7.}$$

For each projection view, if the chosen tube potential is the most dose-efficient one for achieving the desired CNR defined in the reference tube potential, then the total radiation dose is the least. This can be likened to automatic tube current modulation, where the tube potential is dynamically modulated during the scan to maintain the same level of CNR for each projection view. However, this strategy does not work well for a number of reasons when applied in a clinical setting. When tube potential is changing during a single scan, the attenuation coefficients of each voxel element also changes as a function of projection angle. In this case, the map of attenuation coefficients, and, thus, the image trying to be reconstructed, becomes a function of projection angle and image reconstruction is made prohibitively difficult due to data inconsistencies. Unless there is a perfect beam-hardening correction for each kV, tube potential modulation cannot be implemented in the same way as tube current modulation. Thus, the strategy of automatic tube potential modulation presented here will assume tube potential does not change in a single scan. However, the general idea of determining the most dose efficient tube potential according to the attenuation level and noise constraint parameter, which is described below, will also work if the tube potential is modulated at each projection angle.

A simplified representation of the subject size can be described by $\Omega_d=\{d_i|i=1,\ldots,N\}$, where $d_i$ is the x-ray path length passing through the isocenter at the i-th projection view. The contrast of a particular material, for example, iodine, calcium, or soft tissue, relative to the background material is denoted as $C(\Omega_d)$, which represents a function of contrast changing with the subject size. Thus, the CNR is given by:

$$CNR(\Omega_d) = \frac{C(\Omega_d)}{\sigma(\Omega_d)}. \qquad \text{Eqn. 8}$$

To find the most dose efficient tube potential that gives the desired CNR for a given subject size $\Omega_d$, the desired CNR as defined by the reference tube potential and radiation dose for subject size $CNR(\Omega_d,kV_{ref},D_{ref})$ may be considered. Thus, the tube potential that uses the lowest radiation dose to achieve the same value of CNR can be expressed as:

$$\underset{kV}{\operatorname{argmin}} D(\Omega_d, kV, CNR). \qquad \text{Eqn. 9}$$

This objective may also be expressed in another way by considering which tube potential yields the minimum D under the following condition:

$$CNR(\Omega_d,kV,D)=CNR(\Omega_d,kV_{ref},D_{ref}) \qquad \text{Eqn. 10.}$$

This equation may be rewritten to give:

$$\sigma(\Omega_d, kV, D) = \frac{C(\Omega_d, kV)}{C(\Omega_d, kV_{ref})}\sigma(\Omega_d, kV_{ref}, D_{ref}). \qquad \text{Eqn. 11}$$

Therefore, by assuming $\sigma^2(\Omega_d,kV,D)=k(\Omega_d,kV)/D$ where $k(\Omega_d,kV)$ is a coefficient that can determined experimentally, the following can be determined:

$$D = \left[\frac{C(\Omega_d, kV_{ref})}{C(\Omega_d, kV)}\right]^2 \frac{k(\Omega_d, kV)}{k(\Omega_d, kV_{ref})} D_{ref}. \qquad \text{Eqn. 12}$$

A relative dose factor (RDF) that represents the relative dose at a tube potential can be defined. The RDF can also be related to dose efficiency $\epsilon$ for a specific subject size and a desired image quality index can be defined therewith. For example, as shown above, when the CNR is used as an image quality index, RDF is defined to be:

$$RDF(\Omega_d, kV) = \left[\frac{C(\Omega_d, kV_{ref})}{C(\Omega_d, kV)}\right]^2 \frac{k(\Omega_d, kV)}{k(\Omega_d, kV_{ref})}; \qquad \text{Eqn. 13}$$

Therefore, the dose for another tube potential to maintain the same CNR as in the reference tube potential is given by the expression:

$$D=RDF(\Omega_d,kV)D_{ref} \qquad \text{Eqn. 14.}$$

With this in mind, it is possible to quantify the relative dose efficiency of a tube potential for an image quality index such as iodine CNR. If, for example, a reference tube potential is 120 kV, then for a subject of size $\Omega_d$, the RDF is 1.2 for 140 kV. This means that 140 kV involves a 20% higher radiation dose to get the same image quality as 120 kV. Likewise, if RDF is 0.5 for 80 kV, then 80 kV involves 50% less radiation dose to get the same image quality as 120 kV.

However, iodine CNR alone is not always a good image quality index, as there are some clinical applications where it undesirable to maintain a constant iodine CNR, for example, situations where noise is excessively high at a lower tube potential, even though contrast enhancement at the lower tube potential is significantly better than at a higher tube potential. Therefore, a general image quality index may be defined as follows so that an additional variable is provided to adjust image noise according to clinical need:

$$CNR(\Omega_d,kV,D) \geq CNR(\Omega_d,kV_{ref},D_{ref})$$

$$\sigma(\Omega_d,kV,D) \leq \alpha\sigma(\Omega_d,kV_{ref},D_{ref}) \qquad \text{Eqn. 15;}$$

where $\alpha$ can be adjusted to allow varying conditions of noise at the reference tube potential. This gives:

$$D \geq \left[\frac{C(\Omega_d, kV_{ref})}{C(\Omega_d, kV)}\right]^2 \frac{k(\Omega_d, kV)}{k(\Omega_d, kV_{ref})} D_{ref} \qquad \text{Eqn. 16}$$

$$D \geq \frac{k(\Omega_d, kV)}{\alpha^2 k(\Omega_d, kV_{ref})} D_{ref}$$

$$D = \max\left\{\left[\frac{C(\Omega_d, kV_{ref})}{C(\Omega_d, kV)}\right]^2, \frac{1}{\alpha^2}\right\} \cdot \frac{k(\Omega_d kV)}{k(\Omega_d, kV_{ref})} D_{ref}.$$

Thus, the RDF at each tube potential for achieving a target image quality can be defined as follows:

$$RDF(\Omega_d, kV) = \max\left\{\left[\frac{C(\Omega_d, kV_{ref})}{C(\Omega_d, kV)}\right]^2, \frac{1}{\alpha^2}\right\} \cdot \frac{k(\Omega_d, kV)}{k(\Omega_d, kV_{ref})}. \qquad \text{Eqn. 17}$$

Referring again to FIG. 2 and particularly, at process block 204, a reference tube potential and a CT scanning technique is selected. For example, on a Siemens scanner this may include the selection of a quality reference mAs (QRM) if automatic tube current modulation CAREDose4D is active. On a GE scanner, this may include the selection of a noise index if AutomA or SmartmA is active. According to the attenuation information provided by the scanned projection radiograph, the scanner can automatically determine the tube current for each projection angle and scan location and obtain the total radiation dose as expressed in $CTDI_{vol}$. If automatic tube current modulation is inactive, then a constant tube current may be used for the scan.

At process block 206, a noise constraint parameter $\alpha$ is selected. It is contemplated that the noise constraint parameter is based on the task of the CT scan being performed. For example, a CT angiogram may involve an iodine CNR with a wide noise constraint, such as $\alpha=1.5-2.0$, which implies that the iodine CNR is equivalent or improved and that the noise is allowed to be 50-100 percent higher than the reference level. For a contrast-enhanced chest, abdomen, and pelvis examination, an iodine CNR with a moderate noise constraint, such as $\alpha=1.1-1.25$, may be used. For a non-contrast chest, abdomen, and pelvis examination an iodine CNR with a tight noise constraint, such as $\alpha=1.0$, may be used and, for CT enterography an iodine CNR with a noise constraint $\alpha=1.2-1.5$ may be used.

At process block 208, RDF is generated based on scan parameters such as the attenuation level and the selected noise constraint parameter. For example, using Eqn. 17 the RDF is calculated for a range of tube potential's based on subject size and the selected noise constraint parameter and reference tube potential. The contrast and noise information, expressed by $C(\Omega_d, kV)$ and $k(\Omega_d, kV)$, respectively, can be determined using mathematical models or lookup tables generated from phantom measurement. Generally, the most dose-efficient tube potential for achieving a desired image quality is given by the tube potential with the smallest RDF. Thus, at process block 210, the tube potential providing the highest relative dose efficiency, that is, the tube potential having the smallest RDF, is selected and the associated radiation dose is determined by multiplying the orginial $CTDI_{vol}$ at the reference tube potential by RDF. An mA setting (mA, mAs, effective mAs, noise index, or quality reference mAs) that yields the $CTDI_{vol}$ at each tube potential is subsequently calculated at process block 212.

At decision block 214, the CT system parameters and scanning time are checked to determine if the dose level is practically achievable using the selected tube potential. If so, a scan using this tube potential is performed at process block 216 and the scan quality reference tube mAs (QRM) or noise index may be adjusted to provide a desired radiation dose level if automatic tube current modulation is used. If, at decision block 214, the dose is not achievable, then the tube potential with the next highest relative dose efficiency, that is, the next smallest RDF value, is selected at process block 218 and its corresponding tube current is calculated at process block 212. If, at decision block 214, this tube potential value is deemed acceptable, then a scan is performed at process block 216 as described above. Otherwise, this cycle continues until an appropriate tube potential is determined.

Thus, the present invention provides a method that directly quantifies the relative dose efficiency at each tube potential and provides a straightforward mechanism for selecting optimal tube potential based on the calculated dose savings, or dose waste, for each tube potential. This allows straightforward and effective dose reduction based on subject size and other scan parameters.

The present invention's generalized image quality index "iodine CNR with noise constraint," takes into account the various image quality requirements of different diagnostic tasks. RDF is generally dependent on the image quality index used to define the target image quality. As with conventional automatic tube current modulation where noise serves as the image quality index and the tube current is modulated to obtain the desired noise level for each attenuation level, an appropriate image quality index is also needed for automatic tube potential selection. Since iodine is the commonly used contrast media in CT, iodine CNR is typically used, either implicitly or explicitly, in existing studies at lower tube potential. In clinical practice, iodine CNR may generally provide a good indicator of image quality for CT angiograms in which iodine-enhanced vessels are of primary interest. However, iodine CNR alone is not appropriate for every diagnostic task. For example, in contrast-enhanced chest/abdominal CT exams, a contrast agent may help visualize some important structures, but provides little contrast enhancement for other structures of interest. In this case, it is generally beneficial to constrain image noise. Using iodine CNR alone as an image quality index for selecting an optimal tube potential in such exams may potentially yield images with excessive image noise and reduced diagnostic confidence. The "iodine CNR with noise constraint" generalized image quality index incorporates such considerations so that noise constraint parameters provides a flexible means of characterizing and accommodating the various image quality requirements of different diagnostic tasks.

In general, the noise constraint parameter a can be used to control the noise level allowed for a new tube potential relative to the reference tube potential. With a tight noise constraint close to 1, the noise should be approximately matched for different tube potential selections and there is limited potential for dose saving at lower tube potential values. With a loose noise constraint, for example, $\alpha=2$, a significantly larger noise level is permitted while the same CNR is maintained due to improved iodine enhancement. Therefore, the radiation dose can be reduced considerably for smaller subject sizes. It is contemplated that noise constraint selection is dependent on clinical application. For iodine-enhanced angiographic study, the vessel visibility is of primary interest. Since the vessel is enhanced better at lower tube potential by iodine contrast, a relatively higher noise level can be tolerated and relatively high noise constraint can be used. Alternately, while the conspicuity of hypo- or hyper-vascular structures is better at lower values of tube potential in iodine-enhanced chest and abdomen CT exams, many other structures with reduced iodine uptake are still of diagnostic interest. Therefore, excessive noise should not be allowed and a relatively tight noise constraint should be applied. The appropriate value of noise constraint parameters for other diagnostic tasks should be carefully evaluated in clinical practice.

When clinically implementing automatic tube potential selection, in addition to selecting an appropriate noise constraint parameter, it is beneficial to select a reference quality mAs level or noise index at the reference tube potential that is appropriate for the diagnostic task at hand. Such steps help avoid excess radiation dose and image noise. These selections can be set up beforehand for each scanning protocol. Based on parameters provided by a user, the automatic tube potential selection method provided by the present method allows the most dose-efficient tube potential to be selected for a given scan.

The present invention provides a system and method to directly quantify the relative dose that is required at each tube potential to achieve a target image quality. Just as with AEC systems, where noise level can serve as the image quality index and the tube current is modulated to obtain the desired noise level, an appropriate image quality index also needs to be defined for automatic tube potential selection. Iodine CNR can be used as the image quality index, since iodine is so commonly used as a contrast agent in CT exams. However, it is generally not an appropriate index for all diagnostic tasks. For example, in routine contrast-enhanced chest/abdominal CT exams, although the increased contrast enhancement at lower-tube potential is helpful for visualizing some important structures, there is little enhancement in other structures that are also of interest in the diagnosis. Therefore, image noise cannot be too high in these type of clinical application. Using iodine CNR alone as an image quality index for selecting optimal tube potential will yield images with too high image noise and jeopardize the diagnostic confidence. Thus, a generalized image quality index, iodine CNR with a noise constraint, is defined in the accordance with the present invention to accommodate different diagnostic tasks that have different image quality requirements. Thus, iodine CNR is a special case of this general quality index. The noise constraint parameter can be continuously adapted for different clinical applications.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for controlling a computed tomography (CT) system to perform an imaging process of a subject, the method comprising the steps of:
    selecting a scanning technique to be performed on a subject during an imaging process and having an associated at least one of an initial tube potential and an initial tube-current-time-product corresponding to a desired image quality level;
selecting a noise constraint parameter related to at least one of a contrast to noise ratio (CNR) and an image quality index to be achieved with the imaging process;
    performing a scout scan using the CT system to determine a characteristic of the subject;
    adjusting at least one of the initial tube potential and the initial tube-current-time-product for the imaging process using information about the scanning technique, the characteristic of the subject, and the noise constraint parameter to create at least one of an adjusted tube potential and an adjusted tube-current-time-product for the imaging process;
    performing the imaging process using the at least one of the adjusted tube potential and the adjusted tube-current-time-product to collect medical imaging data; and
    reconstructing an image of the subject from the medical imaging data.

2. The method of claim 1 wherein the characteristics of the subject include at least one of a size property and attenuation property.

3. The method of claim 1 wherein adjusting at least one of the initial tube potential and the initial tube-current-time-product for the imaging process includes determining the initial tube potential and an associated dose efficiency using the characteristic of the subject and the noise constraint parameter.

4. The method of claim 3 wherein determining the initial tube potential includes:
    generating a relative dose efficiency for a range of tube potentials based on the characteristic of the subject, a selected reference tube potential, and the noise constraint parameter; and
    selecting a tube potential with a desirable relative dose efficiency.

5. The method of claim 4 wherein selecting the tube potential with the desirable relative dose efficiency employs the relationship:

$$RDF(\Omega_d, kV) = \max\left\{\left[\frac{C(\Omega_d, kV_{ref})}{C(\Omega_d, kV)}\right]^2, \frac{1}{\alpha^2}\right\} \cdot \frac{k(\Omega_d, kV)}{k(\Omega_d, kV_{ref})};$$

in which $RDF(\Omega_d, kV)$ denotes a relative dose at a tube potential dose, $C(\Omega_d, kV)$ and $C(\Omega_d, kV_{ref})$ denote contrast levels, $k(\Omega_d, kV)$ and $k(\Omega_d, kV_{ref})$ denote coefficients relating image noise levels to dose levels, $\alpha$ denotes the noise constraint parameter, $\Omega_d$ denotes the characteristic of the subject, and $kV_{ref}$ denotes the selected reference tube potential.

6. The method of claim 5 wherein creating the adjusted tube potential with a desirable relative dose efficiency includes selecting a tube potential with a highest relative dose efficiency by selecting a tube potential with a smallest value of $RDF(\Omega_d, kV)$.

7. The method of claim 4 wherein determining the tube potential with the desirable achievable dose efficiency further includes:
    estimating an expected radiation dose for the initial tube potential; and
    determining if the expected radiation dose is achievable based on the imaging process and a scanning time of the scanning technique.

8. The method of claim 7 wherein determining if the expected radiation dose is achievable includes:
    calculating a tube current necessary to provide the expected radiation dose; and
    determining if the calculated tube current is achievable within the scanning time.

9. The method of claim 1 wherein the characteristics of the subject include particular materials within the subject to be imaged during the imaging process including at least one of iodine, calcium, and soft tissue.

10. A method for controlling a computed tomography (CT) system to perform an imaging process of a subject, the method comprising the steps of:
    selecting a scanning technique to be performed on a subject during an imaging process and having an associated at least one of an initial tube potential and an initial tube-current-time-product corresponding to a desired image quality level;
    performing a scout scan using the CT system to determine a characteristic of the subject;
    analyzing a relative dose factor (RDF) to be delivered to the subject during the scanning technique using a plurality of at least one of tube potentials and tube-current-time-products and the characteristic of the subject;
    selecting at least one of an adjusted tube potential and an adjusted tube-current-time-product for the imaging process based on the analyzing step;
    performing the imaging process using the at least one of the adjusted tube potential and the adjusted tube-current-time-product to collect medical imaging data; and reconstructing an image of the subject from the medical imaging data.

11. The method of claim 10 wherein the RDF is related to a dose efficiency index for a specific subject size and a desired image quality index.

12. The method of claim 10 wherein the RDF is defined by:

$$RDF(\Omega, kV) = \max\left\{\left[\frac{C(\Omega_d, kV_{ref})}{C(\Omega_d, kV)}\right]^2, \frac{1}{\alpha^2}\right\} \cdot \frac{k(\Omega_d, kV)}{k(\Omega_d, kV_{ref})};$$

in which $RDF(\Omega_d, kV)$ denotes a relative dose at a tube potential dose, $C(\Omega_d, kV)$, and $C(\Omega_d, kV_{ref})$ denote contrast levels, $k(\Omega_d, kV)$ and $k(\Omega_d, kV_{ref})$ denote coefficients relating image noise levels to dose levels, $\alpha$ denotes a noise constraint parameter, $\Omega_d$ denotes the characteristic of the subject, and $kV_{ref}$ denotes a reference tube potential.

13. The method of claim 12 wherein selecting the adjusted tube potential includes selecting a tube potential with a highest relative dose efficiency by selecting a tube potential with a smallest value of $RDF(\Omega_d, kV)$.

14. The method of claim 11 wherein the RDF is based on scan parameters of the scanning technique and a selected noise constraint parameter and the noise constraint parameter controls a noise level permitted for a given tube potential relative to a reference tube potential.

15. A method for controlling a computed tomography (CT) system to perform an imaging process of a subject, the method comprising the steps of:
    selecting a scanning technique to be performed on a subject during an imaging process and having an associated at least one of an initial tube potential and an initial tube-current-time-product corresponding to a desired image quality level;
    performing a scout scan using the CT system to determine a characteristic of the subject including at least materials within the subject;
    adjusting at least one of the initial tube potential and the initial tube-current-time-product for the imaging process using information about the scanning technique and the characteristic of the subject to create at least one of an adjusted tube potential and an adjusted tube-current-time-product for the imaging process;
    performing the imaging process using the at least one of the adjusted tube potential and the adjusted tube-current-time-product to collect medical imaging data; and
    reconstructing an image of the subject from the medical imaging data.

16. A computer tomography (CT) imaging system configured to:
    receive an indication of a medical imaging procedure of a subject to be performed using the CT imaging system indicating an initial dose level and a desired image quality level;
    perform a scout scan of the subject in advance of the prescribed medical imaging procedure;
    determine at least one of a reference tube potential and a tube-current-time-product corresponding to the selected dose level and the desired image quality level;
    determine a noise constraint parameter associated with the prescribed medical imaging procedure;
    determine a tube potential for the prescribed medical imaging procedure to be performed and an associated desired dose efficiency using at least one of a characteristic of the subject, the reference tube potential, the tube-current-time-product, and the noise constraint parameter; and
    perform the prescribed medical imaging procedure using the CT imaging system at the tube potential and based on the desired dose efficiency.

17. The system of claim 16 wherein the characteristic of the subject is determined using information acquired from the scout scan.

18. The system of claim 16 analyzing a relative dose factor (RDF) to be delivered to the subject during the medical imaging procedure using a plurality of at least one of tube potentials and tube-current-time-products.

19. The system of claim 18 wherein the RDF is based on scan parameters of the medical imaging procedure and the noise constraint parameter.

20. The system of claim 19 wherein the RDF is defined by:

$$RDF(\Omega_d, kV) = \max\left\{\left[\frac{C(\Omega_d, kV_{ref})}{C(\Omega_d, kV)}\right]^2, \frac{1}{\alpha^2}\right\} \cdot \frac{k(\Omega_d, kV)}{k(\Omega_d, kV_{ref})};$$

in which $RDF(\Omega_d, kV)$ denotes a relative dose at a tube potential dose, $C(\Omega_d, kV)$ and $C(\Omega_d, kV_{ref})$ denote contrast levels, $k(\Omega_d, kV)$ and $k(\Omega_d, kV_{ref})$ denote coefficients relating image noise levels to dose levels, $\alpha$ denotes the noise constraint parameter, $\Omega_d$ denotes the characteristic of the subject, and $kV_{ref}$ denotes the reference tube potential.

* * * * *

UNITED STATES PATENT AND TRADEMARK OFFICE
CERTIFICATE OF CORRECTION

PATENT NO. : 8,903,037 B2  
APPLICATION NO. : 14/183639  
DATED : December 2, 2014  
INVENTOR(S) : Lifeng Yu et al.

Page 1 of 1

It is certified that error appears in the above-identified patent and that said Letters Patent is hereby corrected as shown below:

In the Specification

Column 8, line 33 - "a" should be --α--

Signed and Sealed this
Twenty-first Day of April, 2015

Michelle K. Lee
*Director of the United States Patent and Trademark Office*